United States Patent [19]
Goff et al.

[11] Patent Number: 4,665,902
[45] Date of Patent: May 19, 1987

[54] FLEXIBLE PENILE PROSTHESIS

[75] Inventors: Kathy O. Goff, Somerville; Kenneth Johnsen, Piscataway, both of N.J.

[73] Assignee: C. R. Bard, Inc., Murray Hill, N.J.

[21] Appl. No.: 804,513

[22] Filed: Dec. 4, 1985

[51] Int. Cl.⁴ .............................................. A61F 5/41
[52] U.S. Cl. ...................................................... 128/79
[58] Field of Search ......................................... 128/79

[56] References Cited

U.S. PATENT DOCUMENTS

| | | | |
|---|---|---|---|
| 4,177,805 | 12/1979 | Tudoriu | 128/79 |
| 4,187,839 | 2/1980 | Nuwayser | 128/79 |
| 4,275,724 | 6/1981 | Behrstock | 128/207.14 |
| 4,363,323 | 12/1982 | Geiss | 604/281 |
| 4,522,198 | 6/1985 | Timm et al. | 128/79 |
| 4,593,690 | 6/1986 | Sheridan et al. | 604/281 |

Primary Examiner—Robert P. Swiatek
Assistant Examiner—Cary E. Stone
Attorney, Agent, or Firm—Kane, Dalsimer, Kane, Sullivan and Kurucz

[57] ABSTRACT

A penile erection prosthesis fully implanted in a patient with a tubular section intermediate its ends containing a flexible zone. The flexible zone is formed by a plurality of circumferential grooves having sides of unequal length. The flexible zone contracts lengthwise with the grooves forming reentrant overlapping folds. The flexible zone is axially bendable and has the ability to retain a position without returning to its previous shape.

8 Claims, 3 Drawing Figures

FLEXIBLE PENILE PROSTHESIS

BACKGROUND OF THE INVENTION

This invention relates to a mechanical prosthesis which provides erections for human males who suffer the dysfunction of erectile impotence.

Various implantable devices for achieving penile erection have been developed. These devices are classified as either mechanical or the more recently developed inflatable devices. The inflatable devices involve an implantable hydraulic fluid transfer system where the corpora are inflated and deflated at will in an attempt to closely approximate the physiological state of the penis in its erect and flaccid states.

The inflatable prostheses appear to have excellent potential; however, they presently have shortcomings. For example, the pump and release valves are frequently located in the scrotum, which is one of the body's sites most disposed to post-operative discomfort and infection. Some inflatable devices require one or more minutes of pumping to inflate. Furthermore, extensive surgery is required and both hydraulic and mechanical failures have been experienced.

The mechanical prostheses were originally stiff rods designed to be implanted in the corpora cavernosa to attain penile erection. Although this system provides a longer, thicker and stiffer erectile state, the flaccid state is no longer achievable—the patient has a permanent erection. Furthermore, fractures during intercourse have been experienced with the stiff rods. After fracture the penis is frail and no longer functional for intercourse.

Flexible rods have been developed to overcome the shortcomings of the stiffer rods. Timm in U.S. Pat. No. 3,987,789 describes a prosthesis including an elongated malleable rod portion housed within a generally tubular physiologically inert plastic body. The malleable rod portion enables the prosthesis to be conformed to a variety of shapes by bending or twisting. During intercourse the prosthesis will maintain the penis in a erectile state and afterwards the penis may be positioned and maintained by the user in a convenient, comfortable position. Flexible rods of this type have been successful, however the penis still does not feel physiologically normal. The penis does not bend freely as it naturally does in the flaccid state.

The latest concept in mechanical implants is rods comprised of hinged segments or links. The hinged rods allow the penis to bend more freely.

Finney et al. in U.S. Pat. No. 4,066,073 describes a hinged mechanical penile prosthesis, which is comprised of relatively rigid proximal and distal portions and a flexible intermediate portion.

Tudoriu in U.S. Pat. No. 4,177,805 describes a hinged mechanical penile prosthesis. The special bending joint of this implant is bendable in only one direction from its straightened position.

Another hinged mechanical penile prosthesis is described in the U.S. Pat. No. of Burton et al., 4,392,562. This implant contains a malleable element which may be bent to enable the prosthesis to be conformed to a variety of shapes. This patent contemplates a prosthesis having a bend limiting member possessing a portion that may be a bellows, which specifically limits bending.

SUMMARY OF THE INVENTION

The present invention relates to a penile prosthesis for implantation in a penis. The prosthesis is designed to allow the penis containing the implant to bend more freely into a wide variety of flaccid positions.

The prosthesis includes a flexible zone which is designed so that once the prosthesis is bent it will hold its position without returning to its previous shape until force is applied to change it. Other prostheses with hinges can be bent, but must be held or restrained to maintain the dependent position.

The prosthesis of the present invention provides for volitional control of the erection by simply bending at the hinge point from the dependent position to the erect position for intercourse.

The preferred embodiment of the present invention is a prosthesis having a relatively rigid cylindrically-shaped tip section, a relatively rigid cylindrically-shaped root section, and a tubular section intermediate the tip and root sections. An outer sheath covers the tubular intermediate section.

The tubular intermediate section has a flexible zone formed of a plurality of circumferential folds. The folds comprise circumferential grooves whose sides are of unequal length and are made reentrant and overlapping by lengthwise contraction of the tube.

When the flexible zone is bent or stretched the short segments of the grooves invert or unfold while the long segments remain rigid. The prosthesis maintains its shape until enough force is applied to fold or overlap the short segments back into their contracted position.

These and various other advantages and features of novelty which characterize the invention are pointed out with particularity in the claims annexed hereto and forming a part hereof. However, for a better understanding of the invention, its advantages, and objects attained by its use, reference should be had to the drawings from which form a further part hereof, and to the accompanying descriptive matter, in which there is illustrated and described a preferred embodiment of the invention.

BRIEF DESCRIPTION OF THE DRAWINGS

In the drawings, in which like reference numerals indicate corresponding parts throughout the several views.

DESCRIPTION OF THE PREFERRED EMBODIMENT

Figure 1:
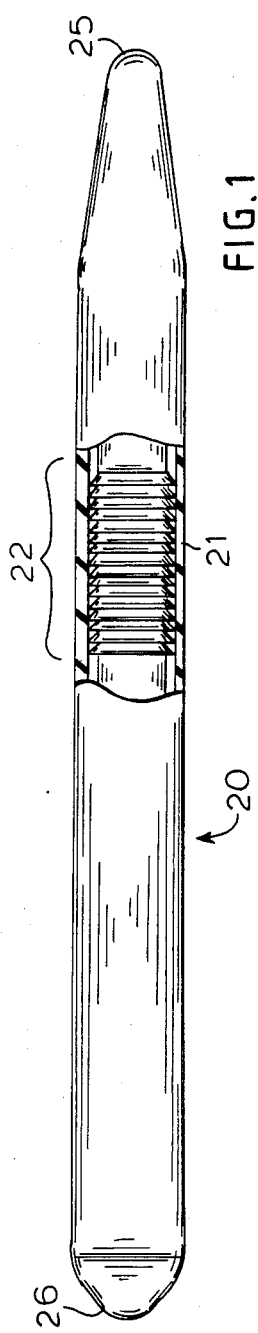
FIG. 1 is a view taken of a preferred embodiment of the present invention in a fully contracted position. A cutaway reveals the flexible zone with overlapping grooves.
Figure 3:
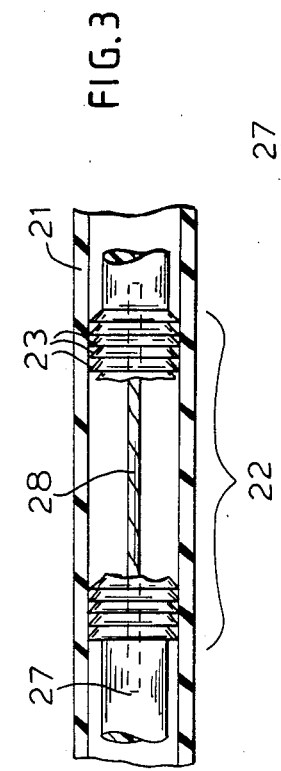
FIG. 3 is a cutaway showing internal tensioning means in the form of an elastic cord to assure proper manipulation of the prosthesis along the flexible zone.

Referring now to the drawings, a preferred embodiment of a hinged mechanical penile prosthesis in accordance with the principles of the present invention is illustrated in FIG. 1, the penile prosthesis generally being referred to by the reference numeral 20. The prosthesis 20 is generally shown as an elongated member with an outer sheath 21 and including a proximal end portion 25, a distal end portion 26, and a flexible zone 22.

The prosthesis 20 of the present invention is designed for implantation, one in each of the corpora cavernosa of the penis by standard surgical procedures for treatment of erectile impotence. The prosthesis 20 is configured to generally match penile corpora cavernosa size so as to extend sufficiently proximally and distally when anchored within the penis and body cavity so as to induce an erected penile state generating sufficient stiffness of the penis for intercourse when stretched and to provide the penis with flaccid characteristics when contracted.

Within the sheath 21 and extending from the proximal end portion and the distal end portion is a tubular member containing the flexible zone 22. The tubular section 27 is contracted lengthwise by applying axially compressive force to the ends of the tube. FIG. 1 shows the prosthesis 20 contracted lengthwise. This position is achieved and held primarily due to the fact that the sides 23 and 24 of grooves are formed of different lengths. When an axially compressive force is applied to the prosthesis 20 and the flexible zone 22 contracts lengthwise with the sides 23 and 24 being placed in a reentrant and overlapping position. When prothesis 20 contracted lengthwise, the sides 23 and 24 overlap thereby forming a plurality of circumferential folds.

Figure 2:
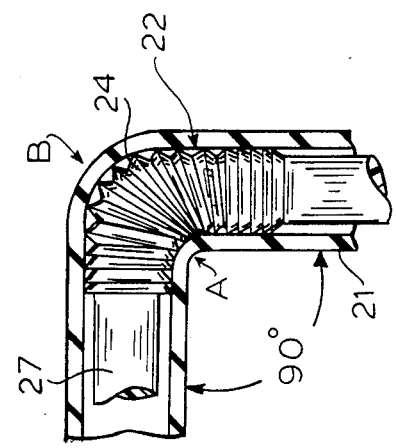
FIG. 2 is a cutaway showing the flexible zone bent representing a flaccid condition.

FIG. 2 shows the prosthesis 20 of the present position in a bent position. This position may be achieved by applying to the prosthesis 20 a manual force in the direction of the desired bend. When this is done, it will be noted that the inner radius A of the flexible zone 22 assumes a different configuration from the outer radius B. The nature of the invention illustrated herein is such that once the prosthesis 20 has been placed in the bent position as illustrated in FIG. 2, it will remain in that position unless a force is applied to unfold the grooves 23 and 24.

In the bent position, the grooves along the inner radius A remain in a folded condition with the sides 23 and 24 overlapping. Along the outer radius B the grooves 23 and 24 become unfolded with sides 23 and 24 disposed from their overlapping position. With the prosthesis bent as indicated in FIG. 2 the portion of the flexible zone 22 along the inner radius A is somewhat further compressed and contracted while the portion along the outer radius B becomes somewhat expanded.

In actual practice, the plurality of circumferential folds sides 23 and 24 of unequal length that are used to form the flexible zone 22 may fail to overlap in the reentrant fashion when the prosthesis 20 is moved from a bent position to a straight position. This problem is most prevalent after long periods of time in the bent or dependent positions. This will prevent the tip section, intermediate section and root section from maintaining coaxial alignment, which is necessary for the device to function optimally. Each fold or convolution in the bendable section snaps into the reentrant position at a slightly different force. As a result of the variations in force required, some convolutions may snap into the reentrant position and then out in a direction opposite to the original bend. This may result in an "S" shape or other irregularly shaped device.

To insure the placement of the folds in the compressed reentrant position, an internal or external axial tensioning means may be included on the cylindrical prosthesis. The internal tensioning means may be an elastic cord 28, spring, or another device capable of maintaining axial tension on the device. The external tensioning means may be incorporated into and be provided by the outer flexible sheath 21 that covers the intermediate bending section. With the tensioning means in use, the device may be moved from the bent position to a straight position consistently, without suffering from the non-axial alignment problems.

It is to be understood, however, even though numerous advantages and characteristics of the invention have been set forth in the foregoing description, together with details of the structure and function of the invention, the disclosure is illustrative only, changes may be made in detail, especially in matters of shape, size and arrangement of parts within the principles of the present invention, to the full extent indicated by the broad general meaning of the terms in which the appended claims are expressed.

What is claimed is:

1. A penile erection prothesis to be fully implantable in a patient, the prosthesis having a relatively rigid tubular middle section intermediate the ends thereof, said middle section having a flexible zone defined by a plurality of circumferential grooves, each of said grooves defined by sides of unequal length, said flexible zone having a plurality of positions, a first position in which said middle section is contracted lengthwise with said middle sides of said grooves reentrant and overlapping and other positions in which said flexible zone is bent about a short axis and a tensioning means for urging the sides of said grooves in a compressed overlapped rentrant position, said tensioning means is a coaxial elastic cord extending across the flexible zone.

2. A penile erection prosthesis of claim 1 wherein said flexible zone being axially bendable with the ability to hold these positions without returning to its previous shape.

3. A penile erection prosthesis according to claim 1 wherein said grooves are identical and extend completely around the periphery of said middle section, each of said grooves having two sides with one of said sides different in length than the other.

4. A penile erection prosthesis according to claim 1 wherein said middle section further comprises a thinwalled, small diameter cylinder having said flexible zone extending over only a minor portion of its length.

5. A penile erection prosthesis according to claim 1 wherein said middle section further comprises a plurality of said flexible zones.

6. A penile erection prosthesis according to claim 1 wherein said reentrant overlapping sides form folds having a component of direction axially of the tube.

7. A penile erection prosthesis according to claim 1 further comprising a relatively rigid cylindrically-shaped tip section having a round end, and a relatively rigid cylindrically-shaped root section having a rounded end.

8. A penile erection prosthesis according to claim 1 wherein the tensioning means is a sheath surrounding the middle section.

* * * * *